United States Patent [19]
Klessig et al.

[11] Patent Number: 6,136,552
[45] Date of Patent: Oct. 24, 2000

[54] HIGH-AFFINITY SALICYLIC ACID-BINDING PROTEIN AND METHODS OF USE

[75] Inventors: Daniel F. Klessig, Bridgewater; He Du, Piscataway, both of N.J.

[73] Assignee: Rutgers, The State University of New Jersey, New Brunswick, N.J.

[21] Appl. No.: 08/956,507

[22] Filed: Oct. 23, 1997

Related U.S. Application Data

[60] Provisional application No. 60/029,806, Oct. 25, 1996.

[51] Int. Cl.⁷ ..................................................... G01N 33/53
[52] U.S. Cl. ......................... 435/7.8; 435/7.23; 435/200; 536/24.1
[58] Field of Search .................................. 435/7.23, 200, 435/7.8; 514/415; 536/24.1

[56] References Cited

U.S. PATENT DOCUMENTS

| | | | |
|---|---|---|---|
| 5,330,897 | 7/1994 | Pindak | 435/7.23 |
| 5,449,615 | 9/1995 | Li et al. | 435/200 |
| 5,654,414 | 8/1997 | Ryalo et al. | 536/24.1 |
| 5,714,509 | 2/1998 | Luo et al. | 514/415 |

FOREIGN PATENT DOCUMENTS

95/12304  5/1995  WIPO .

OTHER PUBLICATIONS

Chen Z, Klessig DF (1991) Identification of a soluble salicylic acid–binding protein that may function in signal transduction in the plant disease resistance response. Proc Natl Acad Sci USA 88: 8179–8183.

Chen Z, Ricigliano JW, Klessig DF (1993a) Purification and characterization of a soluble salicylic acid–binding protein from tobacco. Proc Natl Acad Sci USA 90: 9533–9537.

Chen Z, Silva H, Klessig DF (1993b) Active oxygen species in the induction of plant systemic acquired resistance by salicylic acid. Science 262: 1883–1886.

Conrath U, Chen Z, Ricigliano JW, Klessig DF (1995) Two inducers of plant defense responses, 2,6–dichloroisonicotinic acid and salicylic acid, inhibit catalase activity in tabacco. Proc Natl Acad Sci USA 92: 7143–7147.

Durner J, Klessig DF (1995) Inhibition of ascorbate peroxidase by salicylic acid and 2,6–dichloroisonicotinic acid, two inducers of plant defense responses. Proc Natl Acad Sci USA 92: 11312–11316.

Durner J, Klessig DF (1996) Salicylic acid is a modulator of tobacco and mammalian catalases. J Biol Chem 271: 28492–28501.

Sanchez–Casas, P. et al, Plant Physiol, vol. 106, p 1675–1679, 1994.

Klessig, D. F. et al, Biochem. Soc. Symp., vol. 60, p 219–229, 1994.

Nair, P. M. et al, Indian J. Biochem. Bio–physic., vol. 28(1), p 22–29, 1991.

Goldsbrough, AP et al, Plant. J. (England), vol. 3(4), p563–571, 1993.

*Primary Examiner*—James C. Housel
*Assistant Examiner*—Ginny Allen Portner
*Attorney, Agent, or Firm*—Dann, Dorfman, Herrell and Skillman

[57] ABSTRACT

A high-affinity salicylic acid-binding protein (SABP2) derivable from tobacco and Arabidopsis is disclosed. The tobacco protein has a molecular weight of approximately 25 kDa and reversibly binds SA with an apparent $K_d$ of approximately 90 nM and a $B_{max}$ of 10 fmol/mg protein. The SABP2 of the invention may be used to identify analogues of SA. Analogues so identified may be used in plants to augment disease-resistance response pathways or other SA-sensitive processes in which SA plays a role. Possible examples include flowering and alternative respiration. The SABP2 of the invention may also be used to identify and clone a gene or cDNA that encodes it, which then may be used to generate transgenic plants having altered SABP2 levels.

7 Claims, 11 Drawing Sheets

HIGH-AFFINITY SALICYLIC ACID-BINDING PROTEIN AND METHODS OF USE

This application claims priority from U.S. Provisional Application Ser. No. 60/029,806, filed Oct. 25, 1996 now abandoned.

Pursuant to 35 U.S.C. §202(c), it is acknowledged that the U.S. Government has certain rights in the invention described herein, which was made in part with funds from the National Science Foundation, Grant Nos. MCB-9310371 and MCB-9514239.

FIELD OF THE INVENTION

This invention relates to proteins involved in signal transduction pathways in higher plants. More specifically, the invention relates to a novel protein involved in stress and disease resistance pathways in multicellular plants. The proteins of the invention may be used to advantage to identify novel salicylic acid (SA) analogues. Isolated nucleic acids encoding the proteins will be useful to alter the SA signal transduction pathway in plants.

BACKGROUND OF THE INVENTION

Several publications are referenced in this application by author name and year of publication in parentheses in order to more fully describe the state of the art to which this invention pertains. Full citations for these references are found at the end of the specification. The disclosure of each of these publications is incorporated by reference herein.

Plants can respond to infection by microbial pathogens through the activation of a variety of defense responses. At the sites of infection, a hypersensitive response (HR) is often initiated. The hallmark of this response is the formation of necrotic lesions, a process that is likely due to programmed host cell death. In addition, associated with the HR is the restriction of pathogen growth and spread. Frequently, defense responses are also activated in tissue distal to the sites of infection according to a phenomenon known as systemic acquired resistance (SAR). Development of SAR results in an enhanced and long-lasting resistance to secondary challenge by the same or even unrelated pathogens. Associated with both HR and SAR is the expression of pathogenesis-related (PR) genes, several of whose products have been shown to have antimicrobial activity (for review, see Ryals et al., 1994; Klessig and Malamy, 1994; Wobbe and Klessig, 1996).

A mounting body of evidence tends to indicate that salicylic acid (SA) plays a key role in the activation of certain defense responses in a number of dicotyledonous species. For example, rises in endogenous SA levels correlate with the induction of PR genes and development of resistance in tobacco and cucumber (Malamy et al., 1990 and 1992, Métraux et al., 1990; Rasmussen et al., 1991). In addition, several mutants of Arabidopsis (e.g., cpr, lsd, acd) have been isolated which constitutively express PR genes and show enhanced resistance. They also demonstrate elevated levels of SA (Bowling et al., 1994; Dietrich et al., 1994; Greenberg et al., 1994). Conversely, Arabidopsis mutants defective in SA signal transduction (e.g., npr, nim, sai) exhibit enhanced susceptibility to pathogens (Cao et al., 1994; Delaney et al., 1995; Shah et al., 1996). Exogenously applied SA also induces PR gene expression and enhanced resistance in tobacco (White, 1979; Antoniw and White, 1980) and a variety of other plants (for review, see Klessig and Malamy, 1994). Furthermore, transgenic Arabidopsis and tobacco that express the bacterial salicylate hydroxylase (nahG) gene, whose product converts SA into biologically inactive catechol, fail to develop SAR and show increased susceptibility to primary infections by both virulent and avirulent pathogens (Gaffney et al., 1993; Delaney et al., 1994).

During the past several years, attempts to elucidate the mechanisms of SA action in plant disease resistance have been made by identifying the cellular components with which SA interacts. Initial studies led to the identification of a SA-binding protein that was later shown to be a catalase. Further analysis demonstrated that SA inhibited tobacco catalase activity in suspension cells and in crude leaf extracts. SA also inhibited the purified enzyme (Chen et al., 1993b; Conrath et al., 1995; Durner and Klessig, 1996). Thus, it was proposed that increases in SA after pathogen infection might inhibit catalase activity, producing elevated levels of $H_2O_2$ that could activate certain defense responses, including PR gene expression. Supporting this hypothesis was the observation that prooxidants induced PR-1 gene expression (Chen et al., 1993b), while antioxidants suppressed the SA-mediated expression of PR-1 genes (Conrath et al., 1995; Chen Z, Liu Y, Conrath, U. and Klessig, D. F., unpublished data). In addition, the other major $H_2O_2$-scavenging enzyme, ascorbate peroxidase (APX), was subsequently shown to be inhibited by SA (Durner and Klessig, 1995).

In contrast, several recent studies have questioned the role of $H_2O_2$ and the SA-mediated inhibition of catalase and APX during the activation of defense responses. No detectable increases in $H_2O_2$ levels were found during the establishment of SAR (Neuenschwander et al., 1995) and significant reductions in catalase activity were not observed in tobacco infected with Pseudomonas syringae or in leaf discs pretreated with SA (Bi et al., 1995). In addition, $H_2O_2$ and $H_2O_2$-inducing chemicals were unable to induce PR-1 gene expression in NahG transgenic plants (Bi et al., 1995; Neuenschwander et al., 1995). Moreover, high concentrations of $H_2O_2$ (150 mM–1000 mM) were shown to induce SA accumulation (Neuenschwander et al., 1995; León et al., 1995; Summermatter et al., 1995). Finally, trangenic plants having significantly lower catalase activity via transformation with catalase antisense or cosuppressing sense constructs, did not exhibit constitutive PR-1 gene expression unless there was concurrent development of necrosis (Chamnonpol et al., 1996; Takahashi et al., 1997). From these results it appears that $H_2O_2$ acts upstream of SA in the signal transduction cascade rather than, or in addition to, acting downstream of SA.

Taken together, these studies suggest that the activation of defense responses is mediated through the interaction of SA with other cellular factors, rather than, or in addition to interactions with catalase and APX. To date, these other cellular factors have not yet been isolated. An advance in the art of genetically engineered disease resistance in plants would be obtained by identifying and characterizing cellular factors involved in plant defense responses, particularly in SA-mediated responses.

SUMMARY OF THE INVENTION

This invention provides a novel high-affinity salicylic acid-binding protein (SABP2), which is involved in the SA-mediated signal transduction pathway leading to disease defense responses in plants.

According to one aspect of the invention an isolated protein is provided, which reversibly binds SA. The protein has an apparent molecular mass of less than 50 kDa (specifically between about 10 and 40 kDa and most specifically about 25 kDa for the tobacco protein) as determined by gel filtration chromatography. In a preferred embodiment, the protein binds to SA with a $K_d$ of less than about 500 nM (preferably between about 50 and 250 nM) and has a $B_{max}$ (concentration of binding sites) for SA of less than about 100 fmol/mg protein, preferably about 10 fmol/mg protein.

In preferred embodiments of the invention, the above-described protein is isolated from a plant, such as tobacco or Arabidopsis.

According to another aspect of the invention, antibodies immunologically specific for part or all of the protein of the invention are provided.

According to another aspect of the invention, an isolated nucleic acid having a coding sequence that encodes part or all of the protein of the invention is provided.

According to another aspect of the invention, transgenic plants comprising SABP2-encoding nucleic acids, or portions thereof, are provided.

According to another aspect of the invention, a method of identifying analogues of SA is provided. The method includes the following steps: (a) providing a control sample and a series of test samples, each in a known volume of assay buffer, each sample comprising (i) an equivalent amount of SABP2 protein as described above, and (ii) an equivalent amount of detectably labeled SA sufficient to effect maximal binding of the SA to the SABP2 under the selected assay conditions in the control sample; (b) adding to the test samples in the series incrementally increasing, pre-determined amounts of the test compound, the objective being to generate a concentration series for the test compound in the assay that ideally should span an exponential range of concentrations (e.g., 0.0001 μM–10,000 μM); (c) incubating the control sample and the test samples under the same conditions, selected to enable the test compound, if capable, to compete with the detectably labeled SA for binding to the SABP2; and (d) measuring the amount of detectably labeled SA bound to the SABP2 in the control sample and each test sample. An incremental decrease in the amount of SA bound to the SABP2 that is concomitant with the incremental increase in amount of test compound in each of the test samples, as compared with the control sample, indicates that the test compound may be a functional analogue of SA. The concentration of the test compound required to achieve half-maximal inhibition of labeled SA binding to SABP2 (i.e., the $IC_{50}$), provides further information as to the compound's ability to act as a functional analogue of SA. Compounds exhibiting $IC_{50}$ values similar to SA or its known biologically active analogues (see FIG. 6 below) would be good candidates for further investigation as to their ability to serve as functional SA analogues.

Other features and advantages of the present invention will be understood by reference to the detailed description of the invention and examples set forth below.

BRIEF DESCRIPTION OF THE DRAWINGS

FIG. 3A shows a comparison of total binding (▲) and nonspecific binding (○) with increasing concentrations of [$^3$H]SA. Specific binding (•) was calculated by subtracting nonspecific binding from the total binding.

FIG. 4A shows total [$^3$H]SA-binding activity (■) and nonspecific binding activity (□) as measured by a standard binding assay.

FIG. 7A shows a northern blot analysis of PR-1 mRNA levels 24 hours after SA and BTH treatment. As a control, rRNA present in each lane is also shown.

DETAILED DESCRIPTION OF THE INVENTION

I. Definitions

Figure 1:
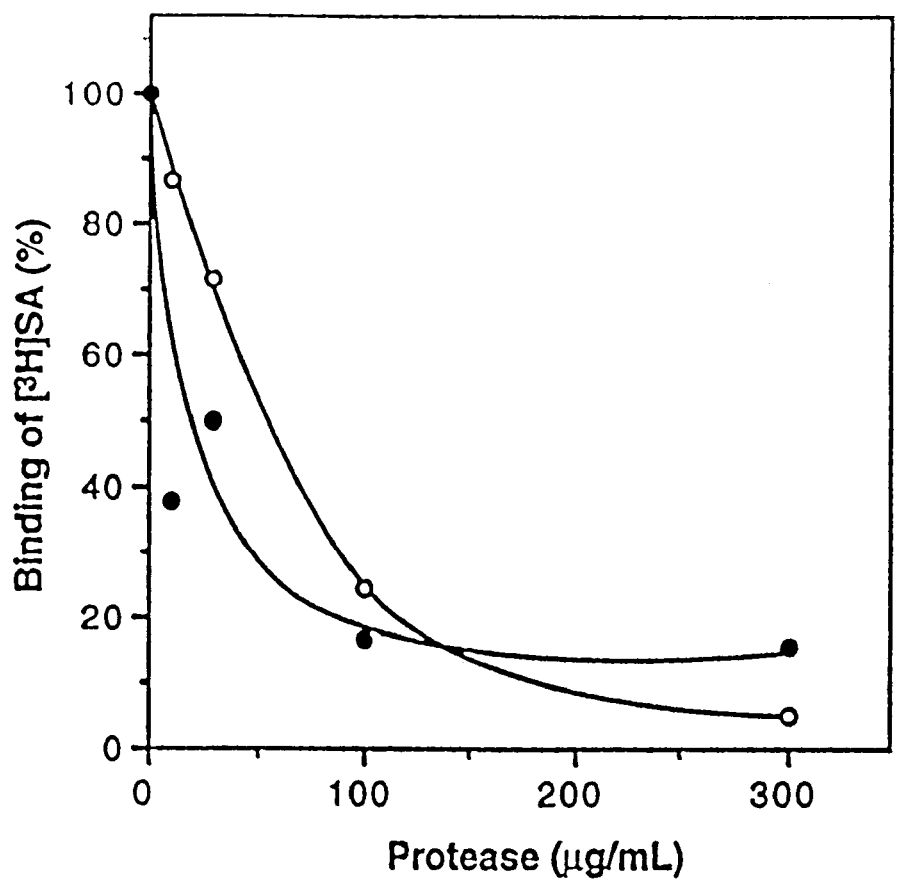
FIG. 1 is a graph depicting the effect of protease digestion on the binding activity of the 50–75% $(NH_4)_2SO_4$ fraction of a soluble protein extract from tobacco leaves. Aliquots of the 50–75% fraction were incubated with various amounts of trypsin (•) or pronase (○) at 30° C. for 6 hours. [$^3$H]SA binding was assayed as described in Example 1. Background radioactivity was subtracted and the binding activity of the control (no protease) was used as 100%.

Various terms relating to the biological molecules of the present invention are used hereinabove and also throughout the specifications and claims.

The term "substantially pure" refers to a preparation comprising at least 50–60% by weight the compound of interest (e.g., protein, nucleic acid, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to proteins of the invention, the term "isolated protein" or "isolated and purified protein" is sometimes used herein. This term may refer to a protein which has been sufficiently separated from other proteins with which it would naturally be associated, so as to exist in substantially pure form (as defined above). This term may also refer to a protein produced by expression of an isolated nucleic acid molecule encoding the protein.

With reference to nucleic acids, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a substantially pure form (as defined above).

With respect to antibodies, the term "immunologically specific" refers to antibodies that bind to one or more epitopes of a protein of interest, but which do not substantially recognize and bind other molecules in a sample containing a mixed population of antigenic biological molecules.

The term "specifically hybridizing" refers to the association between two single-stranded nucleotide molecules of sufficiently complementary sequence to permit such hybridization under pre-determined conditions generally used in the art (sometimes termed "substantially complementary"), to the substantial exclusion of hybridization with single-stranded nucleic acids of non-complementary sequence.

The term "pathogen-inoculated" refers to the inoculation of a plant with a pathogen.

The term "disease defense response" refers to a change in metabolism, biosynthetic activity or gene expression that enhances the plant's ability to suppress the replication and spread of a microbial pathogen (i.e., to resist the microbial pathogen). Examples of plant disease defense responses include, but are not limited to, production of low molecular weight compounds with antimicrobial activity (referred to as phytoalexins) and induction of expression of defense (or defense-related) genes, whose products include, for example, peroxidases, cell wall proteins, proteinase inhibitors, hydrolytic enzymes, pathogenesis-related (PR) proteins and phytoalexin biosynthetic enzymes, such as phenylalanine ammonia lyase and chalcone synthase (Dempsey and Klessig, 1995). Such defense responses appear to be induced in plants by several signal transduction pathways involving secondary defense signaling molecules produced in plants. Certain of these defense response pathways are SA dependent, while others are partially SA dependent and still others are SA independent. Agents that induce disease defense responses in plants include, but are not limited to: (1) microbial pathogens, such as fungi, bacteria and viruses; (2) microbial components and other defense response elicitors, such as proteins and protein fragments, small peptides, β-glucans, elicitins and harpins, cryptogein and oligosaccharides; and (3) secondary defense signaling molecules produced by the plant, such as SA, $H_2O_2$, ethylene and jasmonates.

The terms "defense-related genes" and "defense-related proteins" refer to genes or their encoded proteins whose expression or synthesis is associated with (induced after) infection with a pathogen to which the plant is usually resistant.

The term "promoter region" refers to the 5' regulatory regions of a gene (e.g., CaMV 35S promoters and/or tetracycline repressor/operator gene promoters).

The term "reporter gene" refers to a nucleic acid coding sequence that encodes a readily detectable gene product, which may be operably linked to a promoter region to form a chimeric gene, such that expression of the coding sequence is regulated by the promoter and the product of the coding sequence is readily assayed.

The term "selectable marker gene" refers to a gene that when expressed confers a selectable phenotype, such as antibiotic resistance, on a transformed cell or plant.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The term "DNA construct" refers to genetic sequence used to transform plants and generate progeny transgenic plants. These constructs may be administered to plants in a viral or plasmid vector. Other methods of delivery such as Agrobacterium T-DNA mediated transformation and transformation using the biolistic process are also contemplated to be within the scope of the present invention. The transforming DNA may be prepared according to standard protocols such as those set forth in "Current Protocols in Molecular Biology", eds. Frederick M. Ausubel et al., John Wiley & Sons, 1995.

II. Characterization of SABP2

SA is a key component in the signal transduction pathway (s) leading to activation of certain defense responses in plants after pathogen attack. Previous studies have identified several proteins, including catalase and ascorbate peroxidase, through which the SA signal might act. A novel SA-binding protein is described herein, which was identified through the use of a high specific activity ligand, [$^3$H]SA (15–30 Ci/mmole). This soluble protein, referred to as SABP2, differs significantly from a previously-described SABP, which was subsequently shown to be a catalase. For instance, SABP2 is much less abundant in leaf tissue than is catalase, and has an apparent mass ($M_r$) of between about 20 and 40 kDa, as compared with the molecular mass of catalase, which is approximately 240 kDa. The SABP2 from tobacco reversibly binds SA with an apparent $K_d$ of 90 nM, an affinity that is 150 fold higher than that between SA and tobacco catalase.

As described in detail in Example 1, the ability of various analogues of SA to compete with labeled SA for binding to tobacco SABP correlated with their ability to induce defense gene expression and enhanced resistance. Strikingly, benzothiadiazole (BTH), a recently described chemical activator which induces plant defenses and disease resistance at very low rates of application, was the strongest competitor, being much more effective than unlabeled SA. SABP2 protein appears to be involved in signal transduction pathways that are activated during induction of the pathogen resistance pathway in higher plants.

Although the tobacco SABP2 is described and exemplified herein, this invention is intended to encompass proteins from other species that are sufficiently similar to be used interchangeably with tobacco SABP2 for the purposes described below. Accordingly, when the term "SABP2" is used herein, it is intended to encompass all SABP2s having the general physical and functional features described herein, of which tobacco SABP2 is an exemplary member.

The following description sets forth the general procedures involved in practicing the present invention. To the extent that specific materials are mentioned, it is merely for purposes of illustration and is not intended to limit the invention. Unless otherwise specified, general biochemical and molecular biological procedures, such as those set forth in Sambrook et al., *Molecular Cloning,* Cold Spring Harbor Laboratory (1989) (hereinafter "Sambrook et al.") or Ausubel et al. (eds) *Current Protocols in Molecular Biology,* John Wiley & Sons (1997) (hereinafter "Ausubel et al.") are used.

III. Preparation of SAPB2

A SABP2 protein of the present invention may be prepared in a variety of ways, according to known methods. The protein may be purified from appropriate sources, e.g., plant cells or tissues as described in detail in Examples 1 and 2. Those Examples describe the isolation of SABP2 from tobacco leaves, followed by its 26-fold purification by ammonium sulfate fractionation, ion-exchange, hydrophobic-interaction, and gel filtration chromatography.

The availability of the purified protein also enables isolation of a nucleic acid molecule encoding it, using methods commonly known to persons skilled in the art. For instance, a cDNA expression library can be screened with antibodies raised against the purified SABP2. cDNA clones expressing part or all of SABP2 are identified by immunological interaction with the antibodies, and thereafter isolated and characterized (e.g., by restriction mapping and sequencing).

Alternatively, the amino acid sequence of part or all of the SABP2 protein may be determined, and that information used to design oligonucleotide probes for screening cDNA or genomic libraries from appropriate sources, e.g., plant leaves. In a preferred embodiment, the SABP2 protein is treated with a protease, such as trypsin, to produce fragments for amino acid sequence determination. Families of oligonucleotides that encode the amino acid sequence fragments are synthesized, e.g., by the phosphoramadite method employed in the Applied Biosystems 38A DNA Synthesizer or similar devices. These oligonucleotides are used to amplify, by PCR or other amplification methods, cDNA produced by reverse-transcription of plant leaf poly(A)+ RNA. In this manner, cDNA clones encoding part or all of SABP2 can be isolated.

Once nucleic acids molecules encoding SABP2 have been obtained, the SABP2 protein can be produced using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

According to a preferred embodiment, larger quantities of SABP2 may be produced by expression in a suitable procaryotic or eucaryotic system. For example, part or all of a DNA molecule may be inserted into a plasmid vector adapted for expression in a bacterial cell (such as *E. coli*) or a yeast cell (such as *Saccharomyces cerevisiae*), or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, translation control sequences and, optionally, enhancer sequences.

The SABP2 produced by gene expression in a recombinant procaryotic or eucyarotic system may be purified according to methods known in the art. In a preferred embodiment, the recombinant protein contains several (e.g., 6–8) histidine residues on the amino or carboxyl termini, which allows the protein to be affinity purified on a nickel column. If histidine tag-vectors are not used, an alternative approach involves purifying the recombinant protein by affinity separation, such as by immunological interaction with antibodies that bind specifically to the recombinant protein. Such methods are commonly used by skilled practitioners.

The SABP2 of the invention, prepared by the aforementioned methods, may be analyzed according to standard procedures. Methods for analyzing the physical characteristics and biological activity of SABP2 are set forth in Examples 1 and 2.

The present invention also provides antibodies capable of immunospecifically binding to proteins of the invention. Polyclonal or monoclonal antibodies directed toward SABP2 may be prepared according to standard methods. Monoclonal antibodies may be prepared according to general methods of Köhler and Milstein, following standard protocols. In a preferred embodiment, antibodies are prepared, which react immunospecifically with various epitopes of SABP2.

Polyclonal or monoclonal antibodies that immunospecifically interact with SABP2 can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules.

The present invention also provides isolated nucleic acids that encode the SABP2 proteins of the invention. These nucleic acids are obtained using methods, such as those described above, which are routine to persons skilled in the art. Also provided in accordance with the present invention are transgenic plants containing the aforementioned SABP2-encoding nucleic acids, or fragments or derivatives thereof. Such transgenic plants and their utility in disease resistance are described in greater detail below.

IV. Uses of SABP2

As discussed above, the identification, purification and characterization of SABP2 enables use of the protein, or fragments thereof, to clone SABP2-encoding nucleic acid molecules from various plant species. In addition, the purified protein is used to generate polyclonal or monoclonal antibodies, as mentioned above.

SA is a physiologically active compound in plants, animals and microbes. SABP2 almost certainly plays a role in one or more of the physiological effects mediated by SA in plants (see Cutt and Klessig, 1992). SABP2 can be used in biochemical assays for screening for novel, biologically active analogues of SA. As used herein, the term "SA analogue" is intended broadly to refer to functional analogues, instead of or in addition to structural analogues of SA, which can substitute for SA to induce SA-mediated disease defense responses in plants, or other SA-mediated responses (e.g., induction of the alternative oxidase gene or flowering, as described below).

As one example, assays for SA analogues could be based on the ability of analogues to bind SABP2 or to compete with SA for binding to SABP2. A good correlation between binding to SABP2 (measured by competition with labeled SA for binding to SABP2) and biological activity of seven SA analogues for induction of defense responses to microbial pathogens has been demonstrated, as described in Example 1). The observation that BTH, a commercially available synthetic activator of plant defense responses that is more active than SA in inducing defense responses such as PR-1 gene expression, binds SABP2 about 15 fold more avidly than SA, provides compelling support for the utility of this approach. For example, if SABP2 is part of the signal transduction pathway leading to disease resistance, it may be possible to enhance induction of disease resistance using analogues of SA which are not readily metabolized by the plants. It has previously been demonstrated that SA is rapidly conjugated to glucose to form SA β-glucoside (Malamy et al., 1992). This glucoside is not active for induction of disease resistance. Thus a derivative, or analogue of SA that is not readily metabolized, yet binds SABP2 and stimulates the disease resistance response, would be a superior inducer of resistance.

SABP2 likely plays a role in the numerous biological processes shown to be affected by the addition of exogenous SA, including plant disease resistance, thermogenesis and floral development. Thus, these processes may be affected by altering expression levels and/or characteristics of SABP2. Current technologies of genetic engineering make both readily available. In plants, altering the level of SABP2 within the organism can be readily achieved by making transgenic plants that express SABP2 gene under a strong constitutive or inducible promoter in the sense orientation to overproduce SABP2 or in an antisense orientation to disrupt expression of endogenous SABP2 gene(s). For example, if SA and SABP2 are both involved in flower induction, then it is feasible to inhibit flowering by blocking expression of the endogenous SABP2 gene using antisense technology or by blocking function of the endogenous SABP2 by production of a dominant negative mutant form of SABP2. In addition, if SA is a signal for this (or other) process(es), but the signal is not mediated by SABP2, then overexpression of SABP2 gene could also block this process, since SABP2 may act to sequester the SA signal.

In yet another embodiment of the invention, new response systems may be developed in plants, animals and microbes. Introduction of the SABP2 gene under control of an appropriate promoter should facilitate its expression in organisms or tissues in which SABP2 is not normally expressed. These organisms or tissues could then become responsive to SA that is either generated endogenously or applied exogenously. For example, it is possible to genetically engineer the synthesis of SABP2 in specific types of plant tissue (or animal tissue) by using tissue-specific promoters to drive (control) the expression of the SABP2 gene. Some of the tissues may not normally express an endogenous copy of the SABP2 gene or may express the gene at a very low level. Increasing synthesis of SABP2 in this way may affect the host tissue by making the tissue more responsive to SA, without affecting other tissues in which the engineered gene is not expressed. For example, if the amount of SABP2 is a limiting factor in a physiological process such as flower development, then an enhanced production of SABP2 in tissue or cells responsible for flower development could result in greater flower production (and subsequent seed production), without affecting other physiological processes. In another example, the gene encoding SABP2 can be introduced under appropriate control elements into an organism together with a second gene under the control of a promoter which contains a SA responsive element (SARE) that makes it inducible by SA. Such an SARE element from the PR-2d gene has recently been characterized (Shah and Klessig, 1996). The expression of this second gene should then be inducible by application of exogenously applied SA. This simple strategy should be feasible if the SA-SABP2 complex directly activates the SARE-containing promoter. However, if there are other components downstream of SABP2 in the signal transduction pathway, then their presence in the tissue or organism of interest will also be necessary for the system to work. Since SA is relatively innocuous in many systems, particularly animals, and several genes in plants (from which SAREs would be obtained) are highly induced by SA (>100×), this would be an excellent system for inducible high level expression of foreign genes in transformed cells, organisms, or tissues. There is precedence for transfer of inducible gene expression systems between very divergent organisms. For example, the GAL4 system found in yeast has been shown to function in both plants and animals (Ma et al, 1988; Kakidani and Ptashne, 1988).

In another embodiment of the invention, it may be advantageous to alter the binding properties of SABP2 through genetic engineering so that it recognizes and responds to novel SA analogues. For example, a SA-like pathway could be developed including analogues of SA and modified complementary SABP2. This system would parallel the naturally occurring SA signal transduction pathway but is based on discrete and non-competitively binding analogues. In that way, the normal SA-based cellular functions of a plant will continue undisturbed. However, an increase in newly introduced functions can be induced. The engineered plant, containing the modified complementary SABP2 and other downstream mechanisms necessary for SA-induced expression, can be activated by the application of the non-competitive SA analogue. In this embodiment, plant functions would be influenced by two discrete signal transduction systems.

The following examples are provided to illustrate embodiments of the invention. They are not intended to limit the scope of the invention in any way.

EXAMPLE 1

Identification, Partial Purification and Characterization of SAPB2 from Tobacco Leaves Described in this example is the identification of SABP2 in tobacco, using a high specific activity ligand, ([$^3$H]SA, 15–30 Ci/mmol). Partial purification of the SABP2 from a soluble leaf protein extract and characterization of the partially purified SABP2 are also described.

Materials and Methods

Materials. [$^3$H]SA (15–30 Ci/mmol) was custom synthesized by New England Nuclear (DuPont). SA and other benzoic acid derivatives were purchased from Sigma and Aldrich. 2,6-dichloroisonicotinic acid (INA) was generously provided by Uwe Conrath and Heinrich Kauss while benzo (1,2,3)thiadiazole-7-carbothioic acid S-methyl ester (BTH) was obtained as a formulated powder (50% active ingredient) from Stinnes Agrar (Mülheim, Germany). Stock solutions (10 mM) were made by dissolving SA analogues in 20 mM sodium citrate buffer pH 6.5 and kept in dark at 4° C. Trypsin (from bovine pancreas) and pronase (from *Streptomyces griseus*) were purchased from Sigma and Calbiochem, respectively. Antisense catalase transgenic plants (ASCAT1 No. 17; Takahashi et al., 1997) and wild type tobacco plants (cv. Xanthi nc) were grown in growth rooms under 14 hour light cycle at approximately 15,000 lux.

Leaf extraction. Tobacco leaves from 7–8 week old plants (100 g) were deribbed and ground to a fine powder in liquid nitrogen. All subsequent procedures were carried out at 4° C. Soluble proteins were extracted from the powdered leaves by incubating for 30 minutes in 400 mL buffer A containing 20 mM sodium citrate pH 6.5, 5 mM MgSo$_4$, 1 mM EDTA, 14 mM β-mercaptoethanol, and 1% (w/w) polyvinylpyrrolidone (PVP). Cell debris was removed by centrifugation at 23,000 g for 25 minutes and the supernatant was collected by filtration through two layers of Miracloth (Calbiochem). In some preparations the membrane fraction was removed by centrifugation at 85,000 g for 1 hour. Soluble proteins were precipitated from the crude extract with (NH$_4$)$_2$SO$_4$ adjusted sequentially to 25%, 50%, 75%, and 100% saturation, incubated for 30 minutes, and centrifuged at 23,000 g for 25 minutes. Pellets from each (NH$_4$)$_2$SO$_4$ fraction were dissolved in 5 mL buffer A and dialyzed twice in 4 L of buffer A overnight. The four (NH$_4$)$_2$SO$_4$ fraction extracts were stored on ice before use. Catalase activity in the extract was measured using an O$_2$ evolution assay as described by Takahashi et al. (1997). Protein concentration of each extract was measured according to Bradford (Bradford, 1976) using the Bio-Rad protein assay kit.

Protease digestion. Extract (0.5–1.0 mg), in a final volume of 100 μL, was adjusted to pH 8.0 with 10 mM Tris-HCl and 5 mM CaCl$_2$ and 0.01% SDS was added. Digestion was performed by incubating aliquots of the extract with various amounts of protease (0–30 μg) at 30° C. for 6 hours. The digest (100 μL) was buffer-exchanged using a spin column pre-equilibrated in buffer A and the [$^3$H]SA binding assay was then performed as described below.

[3H]SA binding and competition assays. Extracts (50–100 μL of 0.5–50 mg/mL) from various (NH$_4$)$_2$SO$_4$ fractions were mixed with 0.1 μM [$^3$H]SA in 150 μL reaction mixture and incubated on ice for 2 hours. Spin columns were prepared by packing Sephadex G25 gel (exclusion limit 5 kDa; Pharmacia), which was pre-equilibrated in buffer A, in a 1-mL disposable syringe and centrifuging at 1,000 g for 4 minutes at 4° C. This process was repeated until the bed volume of the spin column reached 1 mL. One additional spin with 125 μL buffer A was performed under the same centrifugation conditions. The binding mixture (125 μL) was loaded onto the spin column and immediately centrifuged. Bound [$^3$H]SA in the flow through (100 μL) was measured in a liquid scintillation counter. When no protein extract was included in the binding mixture, the background radioactivity level was 33±3 dpm/100 μL. For the boiling treatment, the extract was boiled for 5 minutes and denatured protein aggregates were removed by centrifugation at 12,000 g for 1 minute. Nonspecific [$^3$H]SA binding was estimated by carrying out the binding assay in the presence of 1 mM unlabeled SA. For the [$^3$H]SA competition assay, unlabeled SA and its analogues were diluted in 20 mM sodium citrate (pH 6.5) and incubated with 50 AL extract and 0.1 MM [$^3$H]SA as described above.

Gel filtration chromatography. The 50–75% (NH$_4$)$_2$SO$_4$ fraction extract was concentrated 10 fold by ultrafiltration using a Centricon-3 concentrator (molecular weight cut off 3 kDa; Amicon). Gel filtration chromatography was carried out at 4° C. using a fast protein liquid chromatography (FPLC) system (Pharmacia). Concentrated extract (200 μL) was loaded onto a Superdex 200 HR 10/30 gel filtration column (separation range 10–600 kDa; Pharmacia) which was pre-equilibrated in buffer A. The column was run in buffer A with a flow rate of 0.5 mL/min. Protein elution from the column was monitored by UV absorbance at 280 nm. One mL-fractions were collected and 150 μL used for [$^3$H]SA-binding assay.

SA-binding protein purification scheme. SABP2 was further purified approximately 26-fold using the following methods. Soluble proteins were extracted from about 400 g tobacco leaves and a 50–75% (NH$_4$)2SO$_4$ fraction was obtained. After dialysis against buffer A overnight, the 50–75% (NH$_4$)$_2$SO$_4$ fraction was adjusted to pH 8.5 with 40 mM Tris-HCl pH 8.5. A DEAE anion-exchange column (Pharmacia; bed volume 35 ml) was pre-equilibrated in 10 mM Bicine pH 8.5 and 1.4 mM β-mercaptoethanol. The adjusted 50–75% (NH$_4$)$_2$SO$_4$ fraction was loaded onto the DEAE column at a flow rate of 1 ml/min. Bound proteins were eluted from the column by the addition of 0.2 M NaCl in 10 mM Bicine pH 8.5 and 1.4 mM β-mercaptoethanol. A FPLC system was used for the following steps of purification. A Butyl Sepharose FF hydrophobic-interaction column (Pharmacia; 20 ml) was pre-equilibrated in 10 mM Tris-HCl pH 7.5, 1 M (NH$_4$)$_2$SO$_4$ and 1.4 mM β-mercaptoethanol. The 0.2 M NaCl DEAE fraction was adjusted to 1 M (NH$_4$)$_2$SO$_4$, and 20 mM Tris-HCl pH 7.5 and loaded onto the butyl Sepharose column at a flow rate of 0.5 ml/min. A linear gradient of 0–100% 10 mM Tris-HCl pH 7.5, 75% ethylene glycol, and 1.4 mM β-mercaptoethanol was applied. Fractions (1 ml) were collected and [$^3$H]SA binding assay was performed on each fraction. Fractions containing

[³H]SA binding activity were pooled. The pooled fractions were concentrated to 200 µl by ultrafiltration using a Centricon-3 concentrator and loaded onto a Superdex 200 HR gel filtration column (Pharmacia) pre-equilibrated in buffer A at a flow rate of 0.5 ml/min. Fractions (1 ml) were assayed for SA binding and active fractions were pooled.

Results

Identification of a SA-binding activity. Using [¹⁴C]SA, a SABP with modest affinity for SA ($K_d$=14 µM has been identified in tobacco leaf extracts; Chen and Klessig, 1991; Chen et al., 1993a). This SABP was later found to be the abundant enzyme catalase (Chen et al., 1993b). To uncover less abundant SABPs, a ligand with much higher specific activity than that used in earlier studies was synthesized. The specific activity of this newly synthesized [³H]SA (24.3 Ci/mmol) was 450 fold higher than that of the [¹⁴C]SA (54.0 mCi/mmol) used previously. Tobacco leaf proteins were extracted in the presence of a reducing agent (β-mercaptoethanol) and the resultant soluble proteins were separated by ammonium sulfate precipitation into four fractions at 0–25%, 25–50%, 50–75%, and 75–100% $(NH_4)_2SO_4$ saturation. Binding assays were then carried out in the presence of 0.1 µM [³H]SA. The 0–25% and the 25–50% $(NH_4)_2SO_4$ fractions contained substantial amounts of binding activity for [³H]SA. However, most of this binding appeared to be nonspecific, as the vast majority remained even in the presence of 1 mM SA (Table 1). While a high concentration of catalase was present in these first two $(NH_4)_2SO_4$ fractions, the ability of the enzyme to bind SA is suppressed under reducing conditions. Therefore, the binding activity observed was most likely non-specific and not due to the presence of catalase (Chen et al., 1993a). The 75–100% fraction contained negligible binding activity. Significantly, the binding activity in the 50–75% fraction was drastically reduced by 85% in the presence of excess unlabeled SA. For the above stated reasons, the 50–75% fraction, which contained the majority of the specific SA-binding activity, was used for further studies.

The nature of the binding activity present in the 50–75% fraction was characterized further. Boiling of the fraction removed over 95% of the binding activity (Table 1). Inclusion of a detergent (0.5% SDS) also reduced binding to 7% of the total binding activity, half the level of nonspecific binding measured in the presence of 1 mM SA. Incubation of this fraction with the proteases pronase or trypsin at 300 µg/mL reduced binding activity by over 80% (FIG. 1), indicating that a protein(s) is likely responsible for binding.

TABLE 1

Binding of [³H]SA to various $(NH_4)_2SO_4$ fraations

| | dpm (×10⁻³) per mg protein from $(NH_4)_2SO_4$ fraction[a] | | | |
|---|---|---|---|---|
| | 0–25% | 25–50% | 50–75%[c] | 75–100% |
| 0.1 µM [³H]SA | 32.8 ± 2.1 | 7.27 ± 0.17 | 2.23 ± 0.24 | 0.35 ± 0.57 |
| [³H]SA + 1 mM SA | 40.7 ± 3.2 | 7.18 ± 0.20 | 0.34 ± 0.01 | 0.35 ± 0.48 |

TABLE 1-continued

Binding of [³H]SA to various $(NH_4)_2SO_4$ fraations

| | dpm (×10⁻³) per mg protein from $(NH_4)_2SO_4$ fraction[a] | | | |
|---|---|---|---|---|
| | 0–25% | 25–50% | 50–75%[c] | 75–100% |
| [³H]SA + 0.5% SDS | ND[b] | ND | 0.15 ± 0.01 | ND |
| [³H]SA + boiling | ND | ND | 0.05 ± 0.01 | ND |

[a]Standard deviation was obtained from three separate measurements. Background radioactivity (see Materials and Methods) was subtracted from the binding activity.
[b]ND, not determined
[c]Total binding activity present in the 50–75% fraction varied from 2.2 × 10³ to 5.5 × 10³ dpm per mg protein in different extracts; non-specific binding accounted for 10–20% of the total binding activity.

Figure 2:
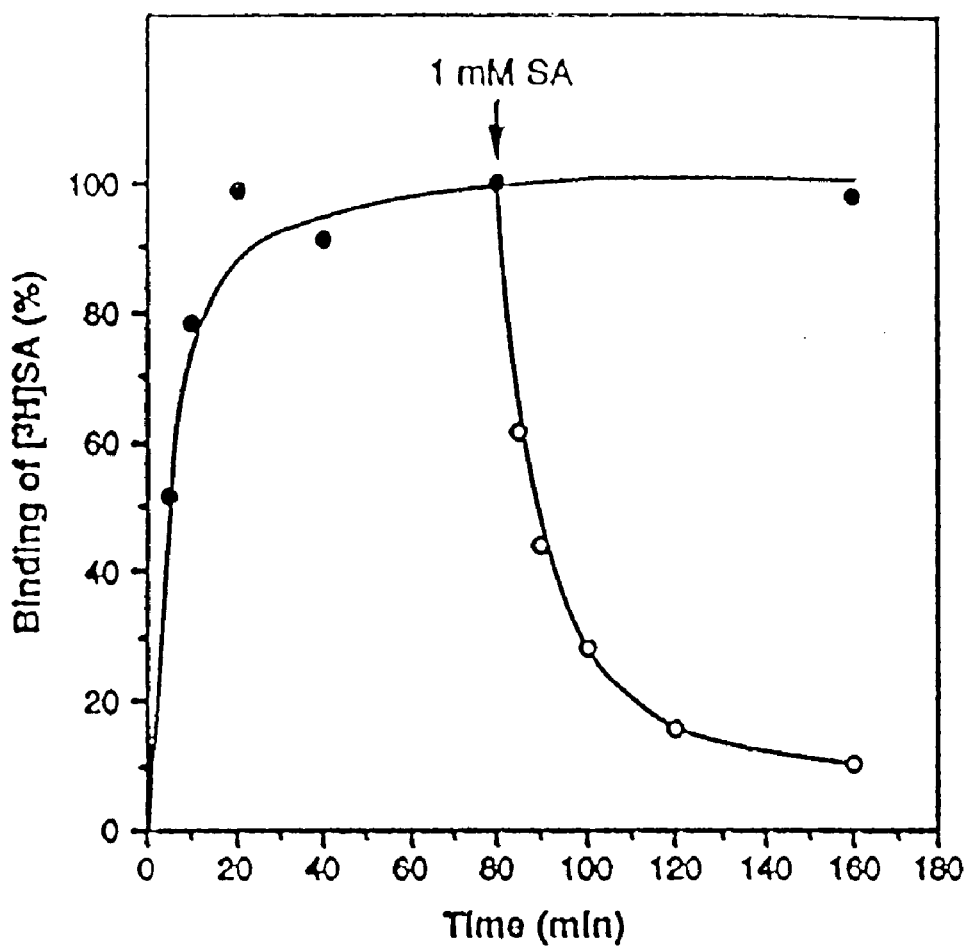
FIG. 2 shows a graph of SABP2 [$^3$H]SA binding kinetics and reversibility. Total [$^3$H]SA binding in the 50–75% fraction (•) reached a maximum within approximately 20 minutes. Binding was reversible as addition of 1 mM SA rapidly reduced [$^3$H]SA binding to 20% within 20 minutes (○). 100% corresponds to the binding activity measured after 160 minutes of incubation.
Figure 3A:
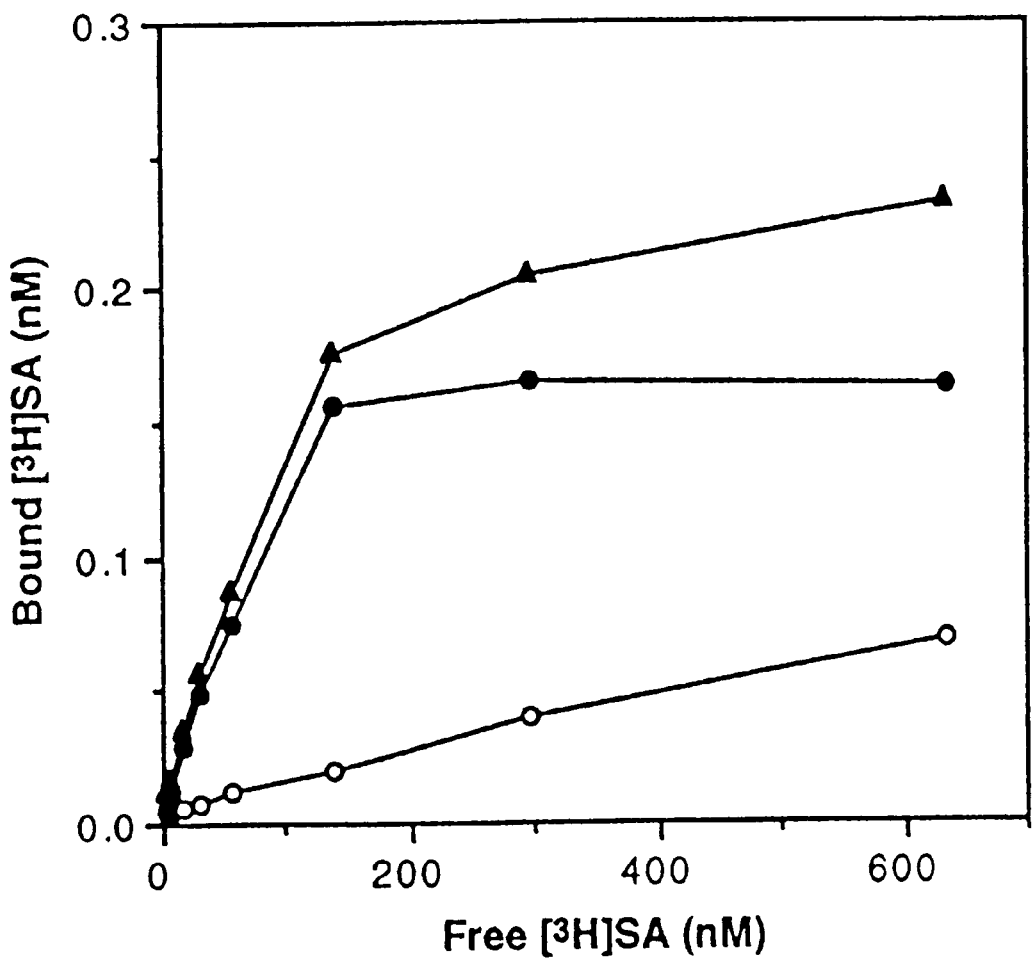
FIGS. 3A+B depicts a pair of graphs illustrating the saturability of [$^3$H]SA binding by SABP2 and a Scatchard plot of the same.
Figure 3B:
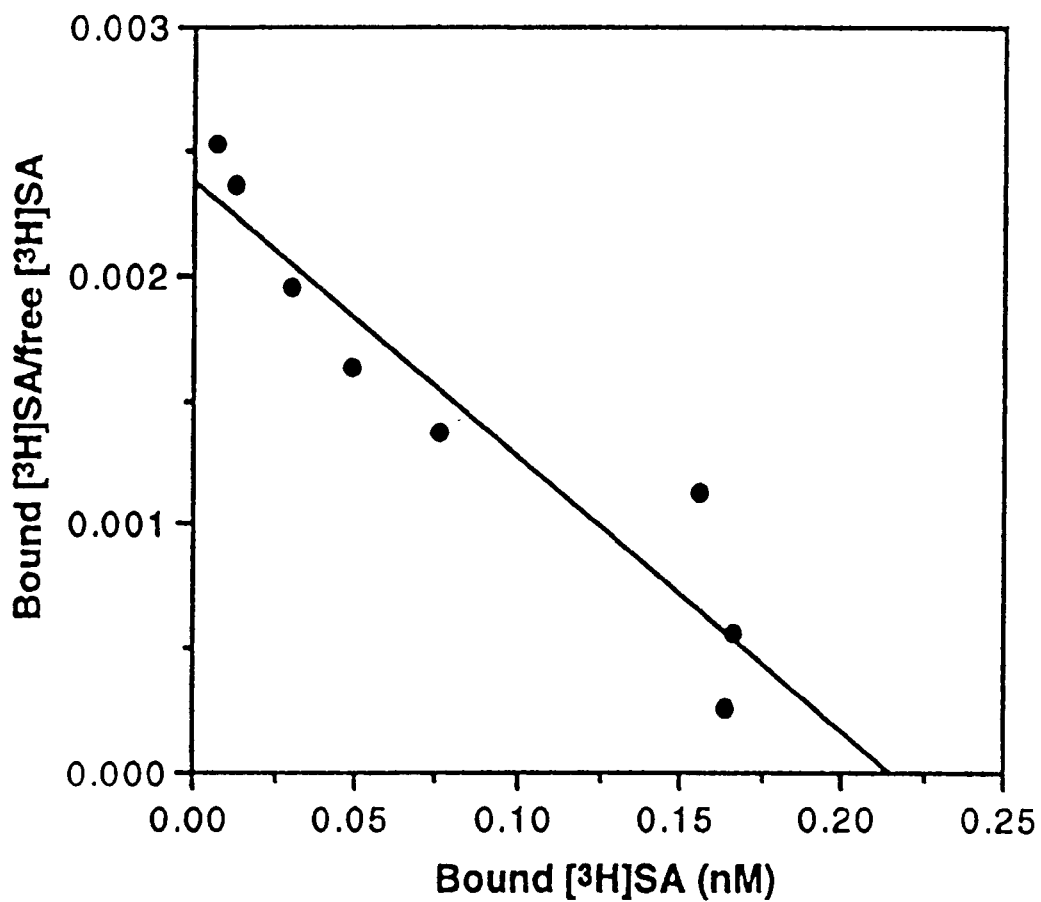
FIG. 3B shows a Scatchard plot of [$^3$H]SA binding. The $K_d$ was 90 nM and $B_{max}$ was 100 fmol/mg protein for the binding activity of the 50–75% fraction. Since the 50–75% fraction contains about one tenth of the total soluble protein in the leaf, the actual $B_{max}$ was 10 fmol/mg protein. The Scatchard plot has been repeated using at least three independent extracts with $K_d$ values ranging from 55 nM to 185 nM.

Characteristics of the SA-binding protein. To further distinguish the novel SA-binding activity identified in the 50–75% fraction from the previously reported SABP (catalase), its binding characteristics were studied. The association of [³H]SA with the novel SABP(s) was rapid (half association time of 5 minutes) and binding was complete within approximately 20 minutes after addition of [³H]SA (FIG. 2). The binding was demonstrably reversible. The addition of 1 mM SA reduced binding to less than 10% with a half dissociation time of 8 minutes (FIG. 2). The binding was saturable with 200 nM or more [³H]SA (FIG. 3A). Scatchard plot analysis of the binding activity revealed a single class of SABP with a $K_d$ of 90 nM and a $B_{max}$ of 10 fmol/mg protein (FIG. 3B). Compared with catalase ($K_d$ of 14 µM and $B_{max}$ of 5 pmol/mg protein; Chen and Klessig, 1991), the SABP present in the 50–75% fraction has a much higher affinity for SA but is present in a much lower amount.

Figure 4A:
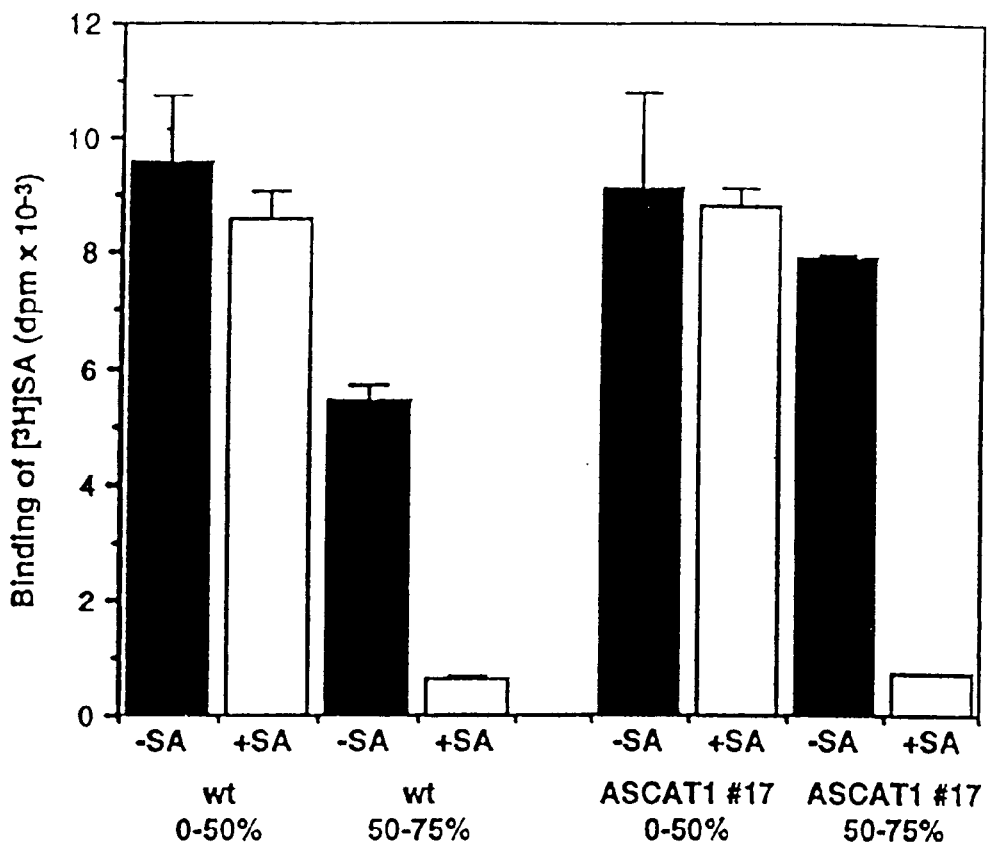
FIGS. 4A+B shows a pair of histograms illustrating SA-binding activity and catalase activity of various ammonium sulfate fractions from wt and ASCAT1 No. 17 transgenic plants.
Figure 4B:
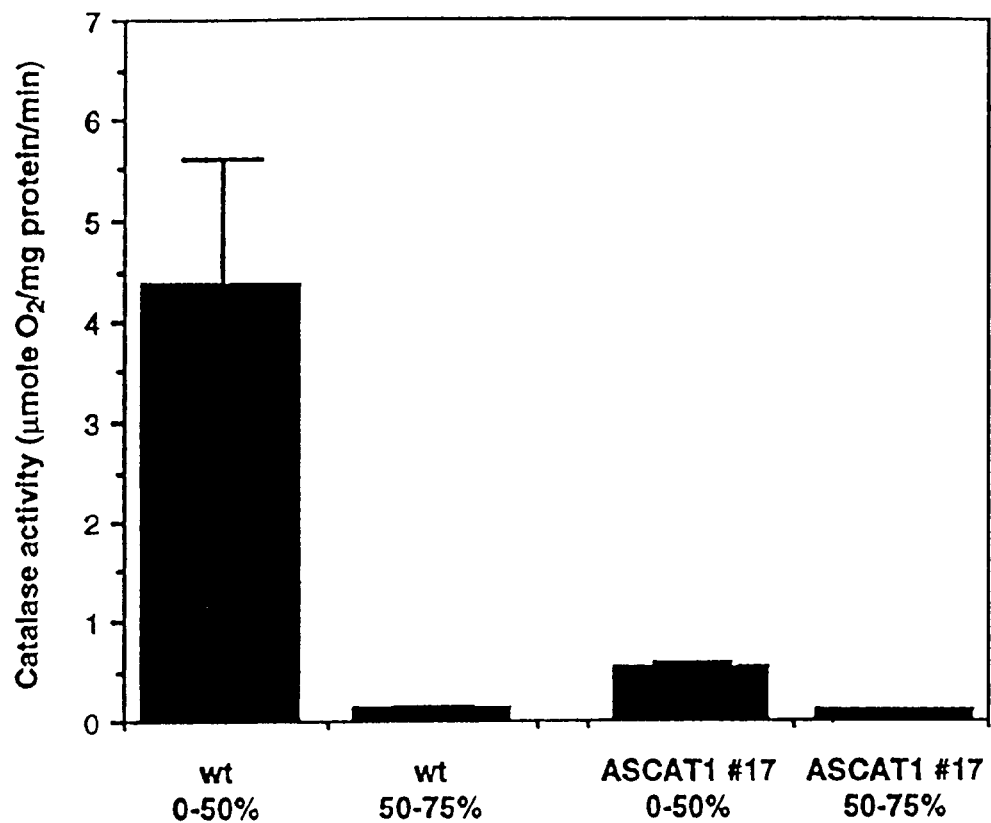
FIG. 4B shows catalase activity as determined by the $O_2$ evolution assay. Standard deviation was determined from three separate measurements.

To unequivocally demonstrate that the new SA binding protein is distinct from catalase, a line of transgenic tobacco plants (ASCAT1 No. 17) was utilized which has greatly reduced level of catalase activity (Takahashi et al., 1997). The 0–50% $(NH_4)_2SO_4$ fractions of both the wild type (wt) plants and the ASCAT1 plants contained similar levels of SA-binding activity (FIG. 4A), although as expected, the ASCAT1 plants had reduced catalase activity (12%) as compared to the wt plants (FIG. 4B). The 50–75% fraction from the wt plants contained little catalase activity (3% of that of the 0–50% fraction) and even less was present in the ASCAT1 plant. However, the SA specific binding activity in the ASCAT1 plants remained as high as in the wt plants. This binding protein has been designated SABP2 to distinguish it from catalase (or SABP1).

Figure 5:
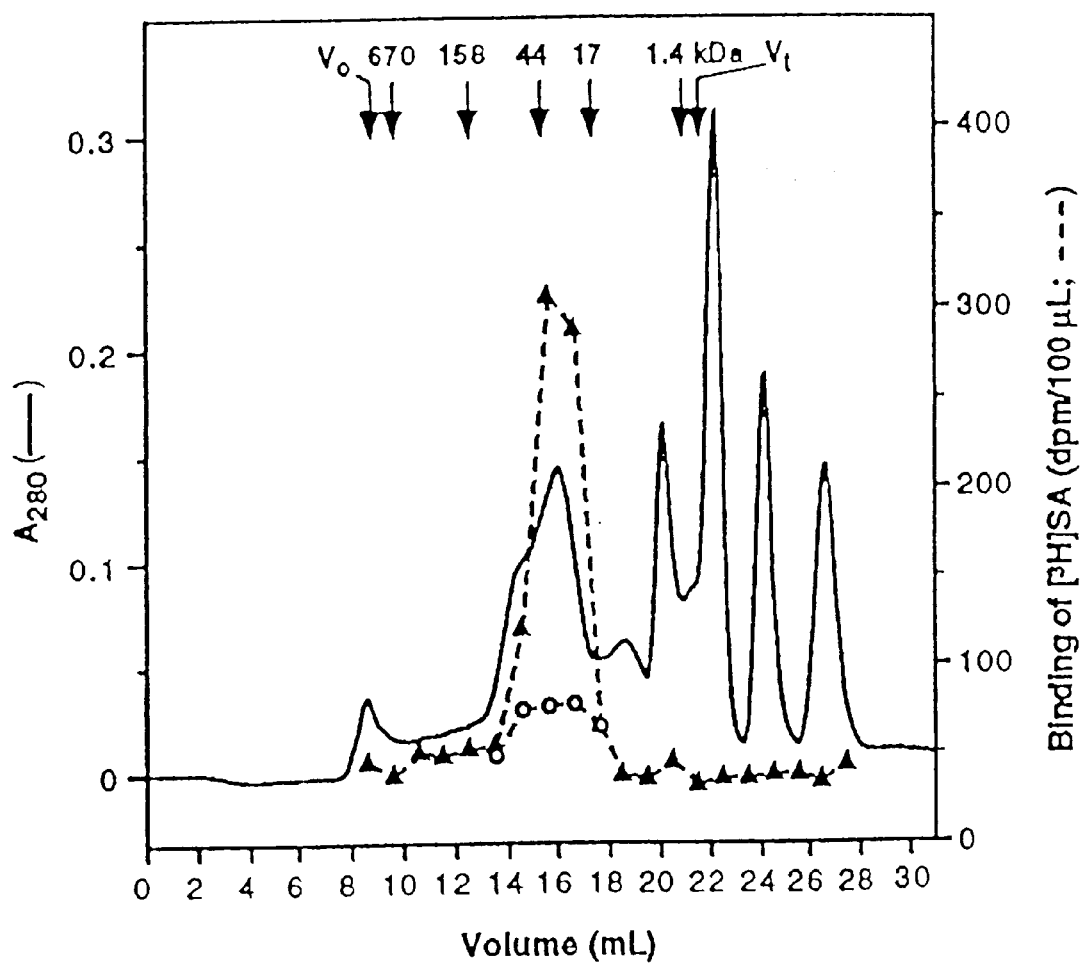
FIG. 5 shows the elution profiles of the 50–75% $(NH_4)_2SO_4$ fraction of a tobacco leaf soluble protein extract following gel filtration chromatography. After concentration to 200 μL the 50–75% fraction was loaded onto a Superdex 200 HR column and the proteins eluted from the column were monitored at 280 nm. Total [$^3$H]SA-binding activity (▲) and nonspecific binding activity (○) were determined for various fractions and plotted as dashed lines. The positions of the molecular mass standards, void volume ($V_0$), and total volume ($V_1$) are indicated at the top of the chromatogram.

To estimate the size of the SABP2, the 50–75% fraction was run on a Superdex 200 gel filtration column, which is capable of separating proteins in the range of 10–600 kDa. A single peak containing SA-binding activity was detected as shown in FIG. 5. This peak corresponds to a protein with an apparent molecular mass ($M_r$) of approximately 25,000. Inclusion of 1 mM SA in the binding reaction inhibited binding to [³H]SA, indicating that binding was specific. To minimize potential ionic interactions between SABP2 and the gel filtration column matrix which could interfere with the size estimation, NaCl (0.2 M) was included in the running buffer and the column was run under the same conditions. The inclusion of NaCl did not change the elution profile of the SA-binding peak.

Figure 6:
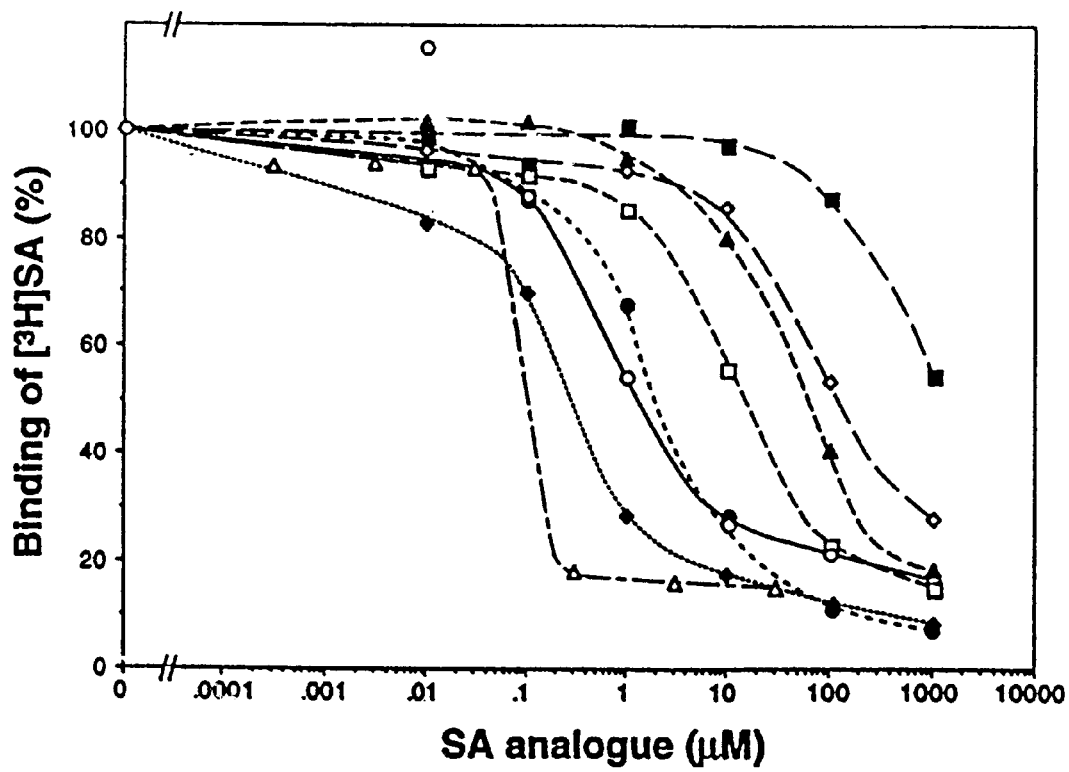
FIG. 6 is a graph showing a competitive binding assay of [$^3$H]SA binding by various SA analogues. Biologically active compounds (SA ○, 5-chloro-SA ◆, 2,6-dihydroxybenzoic acid [2,6-DHBA] ●, 2,6-dichloroisonicotinic acid [INA] ▲, and benzothiadiazole [BTH] △) and biologically inactive compounds (3-HBA ◇, 4-HBA ■, and 2,5-DHBA □) were tested. The binding activity in the absence of SA analogues was used as 100%.

Competition among SA and SA analogues for SABP binding. The biological relevance of SABP2's binding activity was investigated by competition studies using four biologically active and three inactive SA analogues. Active analogues induce PR gene expression and enhanced disease resistance. Although all SA analogues inhibited [³H]SA binding when used at high concentrations such as 1 mM, as shown in FIG. 6, the biologically active analogues (e.g. 5-chlorosalicylic acid (5-CSA) and 2,6-dihydroxybenzoic acid (DHBA) were generally more effective in competing with [³H]SA for binding to SABP2 than the inactive analogues (3-hydroxybenzoic acid [HBA], 4-HBA, and 2,5-DHBA). The active analogues had $IC_{50}$ values at least 10 fold lower than those of the inactive analogues (Table 2). Interestingly, the two functional analogues of SA, INA and the recently reported chemical activator BTH, exhibited marked differences in their ability to compete with [³H]SA. BTH was the most effective competitor with an $IC_{50}$ of 0.1 $\mu$M. This was at least 15 fold lower than that of SA (1.5 $\mu$M). In contrast, INA's $IC_{50}$ (70 $\mu$M) was similar to those of the inactive SA analogues. This finding was surprising, since INA induces defense responses, and the results of genetic (Cao et al., 1994; Delaney et al., 1995; Shah et al., 1996) and biochemical (Conrath et al., 1995; Vernooij et al., 1995; Malamy et al., 1996) studies argue that INA is a functional analogue of SA. One explanation for this apparent discrepancy is that INA must first be converted to an active form in plants. Consistent with this explanation, Métraux and co-workers (1991) demonstrated that labeled INA was partially metabolized to another compound in plants. Our observations that INA effectively blocks tobacco catalase in vivo, but is less effective at inhibiting catalase activity in crude extracts and fails to inhibit purified tobacco catalase (Conrath et al., 1995, Durner and Klessig, 1996), is also consistent with this explanation.

TABLE 2

Correlation between biological activities of
various SA analogues and their $IC_{50}$ of
competition for [³H]SA binding

| | $IC_{50}$ ($\mu$M) | Biological activity[b] |
|---|---|---|
| SA | 1.5 | +[c] |
| 5-chloroSA | 0.3 | + |
| 2,6-dihydroxybenzoic acid | 2.0 | + |
| 3-hydroxybenzoic acid | 105 | −[d] |
| 4-hydroxybenzoic acid | >1000 | − |
| 2,5-dihydroxybenzoic acid | 20 | − |
| INA | 70 | + |
| BTH | 0.1 | + |

Figure 7A:
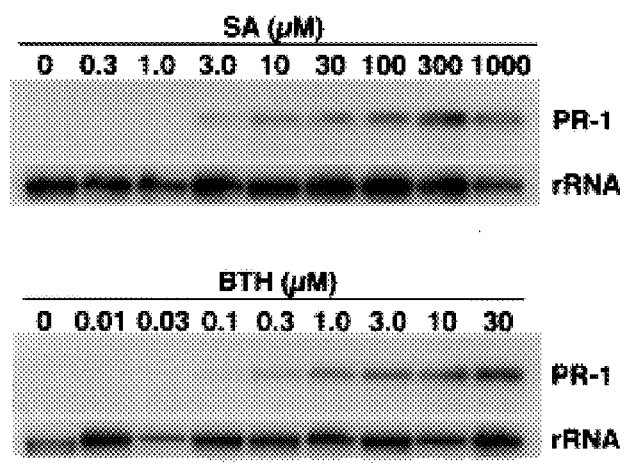
FIGS. 7A+B shows induction of PR-1 gene expression by SA and BTH.
Figure 7B:
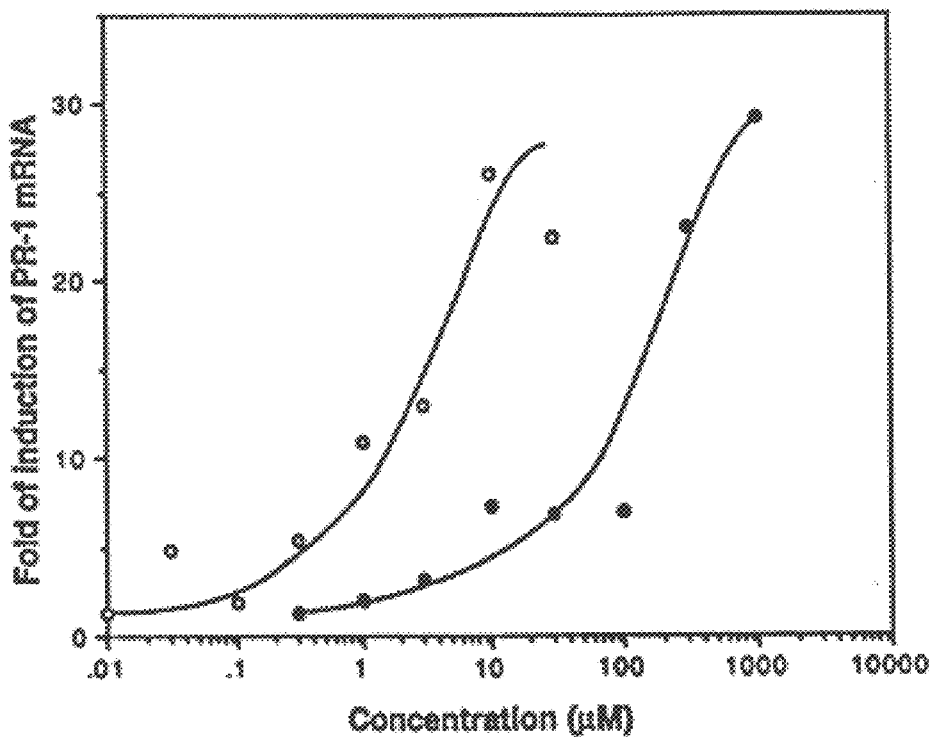
FIG. 7B is a graph showing quantification of the fold-induction of the PR-1 mRNA levels after SA (•) and BTH (○) treatment. The levels of PR-1 mRNA were normalized to the amounts of rRNA. The rRNA-normalized levels of PR-1 mRNA obtained after infiltration of leaf discs with SA or BTH were divided by the rRNA-normalized level of PR-1 mRNA obtained after infiltration with water only to determine the fold induction. The data presented are from a single experiment; two additional experiments were done. The maximum-fold induction of the PR-1 genes and the concentrations of SA and BTH required to reach approximately 50% of this value varied somewhat among the three experiments, depending on the age of the plant. In the three experiments, the concentrations of BTH needed to reach approximately 50% induction were 30- to 40-fold lower than those for SA.

[a]Half maximal concentration at which the SA analogues inhibit 50% of the binding of [³H]SA to the 50–75% fraction ($IC_{50}$) was estimated from the competition assays presented in FIG. 6. Similar results were obtained in a repeat experiment using an independent protein extract.
[b]Biological activities of SA analogues are based on results from FIG. 7 and Abad et al. (1988), Conrath et al. (1995), Friedrich et al. (1996) and Van Loon (1983).
[c]+, active
[d]−, inactive The higher affinity of SABP2 for BTH than for SA was consistent with the greater potency of BTH for induction of the PR-1 genes. At high concentrations of SA or BTH, maximal induction of PR-1 gene expression by SA and BTH was similar (data not shown). However, the dose-response curves for these two activators indicate that BTH is much more effective in inducing PR-1 gene expression (15-fold at approximately 3.3 $\mu$M BTH) than SA (15-fold at approximately 130 $\mu$M SA (FIGS. 7A and 7B).

SABP2 differs markedly from the previously described SABP (Chen and Klessig, 1991; Chen et al., 1993a), which was subsequently shown to be a catalase (Chen et al., 1993b). While both proteins are soluble, they differ in size, abundance, and SA-binding characteristics. SABP2 is present in very low abundance (10 fmol/mg soluble protein; FIG. 3) and has an apparent molecular mass ($M_r$) of approximately 25,000 (FIG. 5). In contrast, catalase, which is a tetramer, has a molecular mass of approximately 240,000 and is a major cellular enzyme. Binding of SABP2 to SA at 0–4° C. approached equilibrium in 15–20 minutes as shown in FIG. 2, versus 90–120 minutes for catalase. Displacement of labeled SA in the presence of excess unlabeled SA was also much more rapid for SABP2 ($t_{1/2}\cong 8$ minutes vs. $t_{1/2}\cong 40$ minutes for catalase). More importantly, SABP2's affinity for SA is approximately 150 fold higher than that of catalase ($K_d$=90 nM vs. 14 $\mu$M;

FIG. 3). Finally, the ASCAT1 No. 17 transgenic line which has severely reduced levels of catalase activity contained similar levels of SA specific binding activity in the 50–75% fraction as the wt plant, as shown in FIG. 4, indicating that SABP2 is distinct from catalase.

An SABP with properties similar to SABP2 has been found in Arabidopsis (data not shown). It also was concentrated in the 50 to 75% $(NH_4)_2SO_4$ fraction. Scatchard-plot analysis indicates that its affinity for SA and abundance are similar to those of the tobacco SABP2.

SABP2's high affinity for SA and very low abundance suggest that it may function as a receptor for this ligand. With a $K_d$ of 90 nM, the affinity of SABP2 for SA is high enough to allow effective binding even in tissues distal to the sites of infection, where only low levels of SA accumulate (0.5–9 $\mu$M; Malamy et al., 1990; Enyedi et al., 1992; Vernooij et al., 1994). Thus, SABP2 is more likely to play a role in SA signaling than are catalase and APX, which require SA levels in the range of 50–300 $\mu$M for effective inhibition of their activities (Chen et al., 1993b; Durner and Klessig, 1995 and 1996). However, a role for catalase (and APX) in SAR, or at the site of initial infection where SA levels approach 100–150 $\mu$M, can not be excluded.

The binding specificity of SABP2 for SA and its analogues is also consistent with a role in disease resistance. Analogues that were biologically active for induction of PR genes and enhanced resistance were 10–200 times more effective at competing with [³H]SA for binding SABP2 than inactive analogues (FIG. 6, Table 2). Moreover, the chemical activator BTH, which is much more active than SA for inducing SAR genes, including PR-1 (FIG. 7; Görlach et al., 1996), and enhanced resistance to pathogens (Görlach et al., 1996), competed approximately 15-fold better than SA for SABP2 binding. However, it should be noted that BTH is also a more effective inhibitor of catalase than SA (J. Durner and D. F. Klessig, unpublished data). Thus, the difference in responsiveness of these two proteins to BTH versus SA cannot be used as an indicator of which is more likely to play a role in disease resistance.

Although the known properties of SABP2 are consistent with it functioning as a receptor or primary target of SA during defense signaling, alternative possibilities need to be considered. SABP2 may play a role in the transport or metabolism of SA. Alternatively, SABP2 might be involved in another SA-mediated process instead of, or in addition to, defense signaling. For example, SA inhibits catalase and APX activities, which in turn may lead to higher $H_2O_2$ levels and the production of SA radicals. The elevated levels of $H_2O_2$, in addition to acting upstream and/or downstream of SA in the defense signal transduction cascade, may also play a role in inducing the alternative oxidase gene, whose product is a key enzyme in alternative respiration and thermogenesis (Wagner, 1995; Vanlerberghe and McIntosh, 1996). SA may also induce the alternative oxidase gene by inhibiting aconitase (Ruffer et al., 1995), which leads to the accumulation of citrate, aconitase's substrate and an effective inducer of the alternative oxidase gene (Vanlerberghe and McIntosh, 1996). Similarly, SA inhibition of 1-aminocyclopropane-1-carboxylic acid oxidase, a key enzyme in ethylene biosynthesis may reduce senescence and ethylene production (Leslie and Romani, 1988). Thus, multiple cellular factors appear to interact with SA to produce a wide variety of effects.

EXAMPLE 2

FURTHER PURIFICATION OF TOBACCO SABP2

Figure 8:
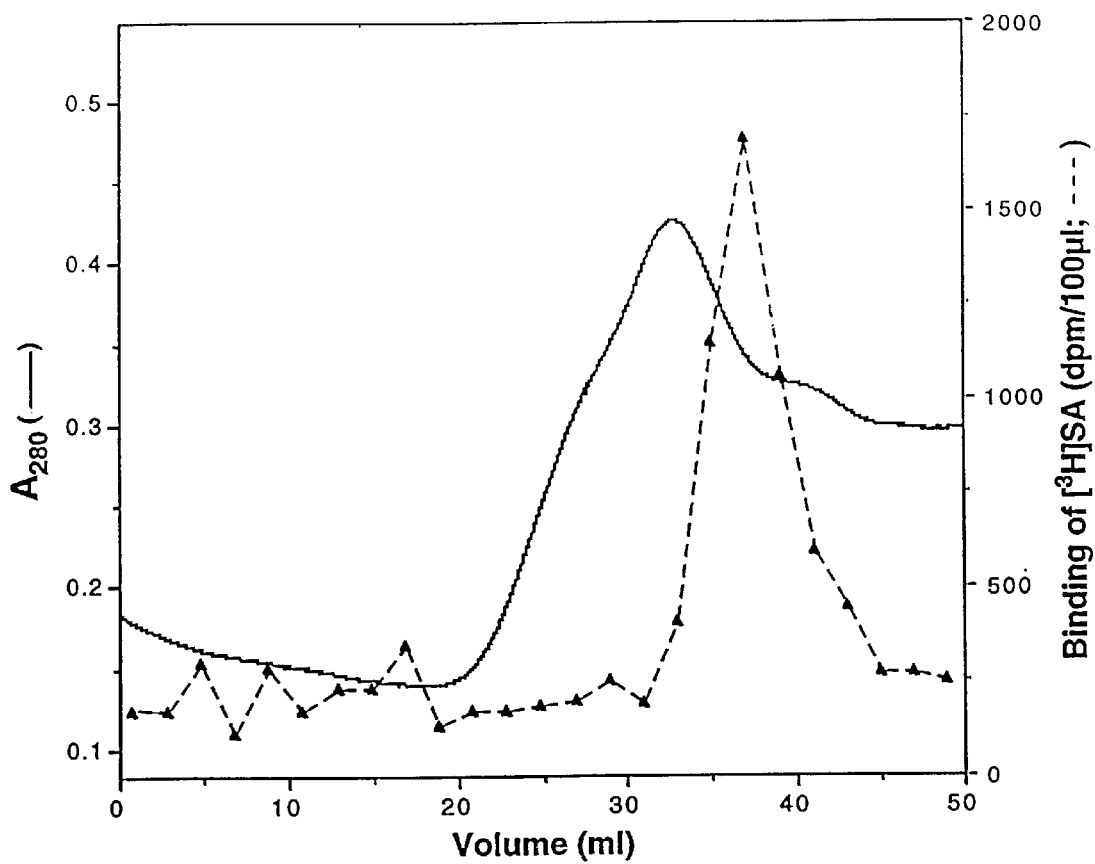
FIG. 8 is a graph depicting the elution profiles of the 0.2 M NaCl DEAE fraction following hydrophobic-interaction chromatography. The 0.2 M NaCl DEAE fraction was adjusted to 1 M $(NH_4)_2SO_4$ and 20 mM Tris-HCl (pH 7.5) and loaded onto a Butyl Sepharose FF column pre-equilibrated in 10 mM Tris-HCl (pH 7.5), 1 M $(NH_4)_2SO_4$ and 1.4 mM β-mercaptoethanol. The column was eluted with a linear gradient of 0–100% 10 mM Tris-HCl pH 7.5, 75% ethylene glycol, and 1.4 mM β-mercaptoethanol. Proteins eluted from the column were monitored at 280 nm. Total [$^3$H]SA binding activity (▲) was determined for each fraction and plotted as a dashed line.
Figure 9:
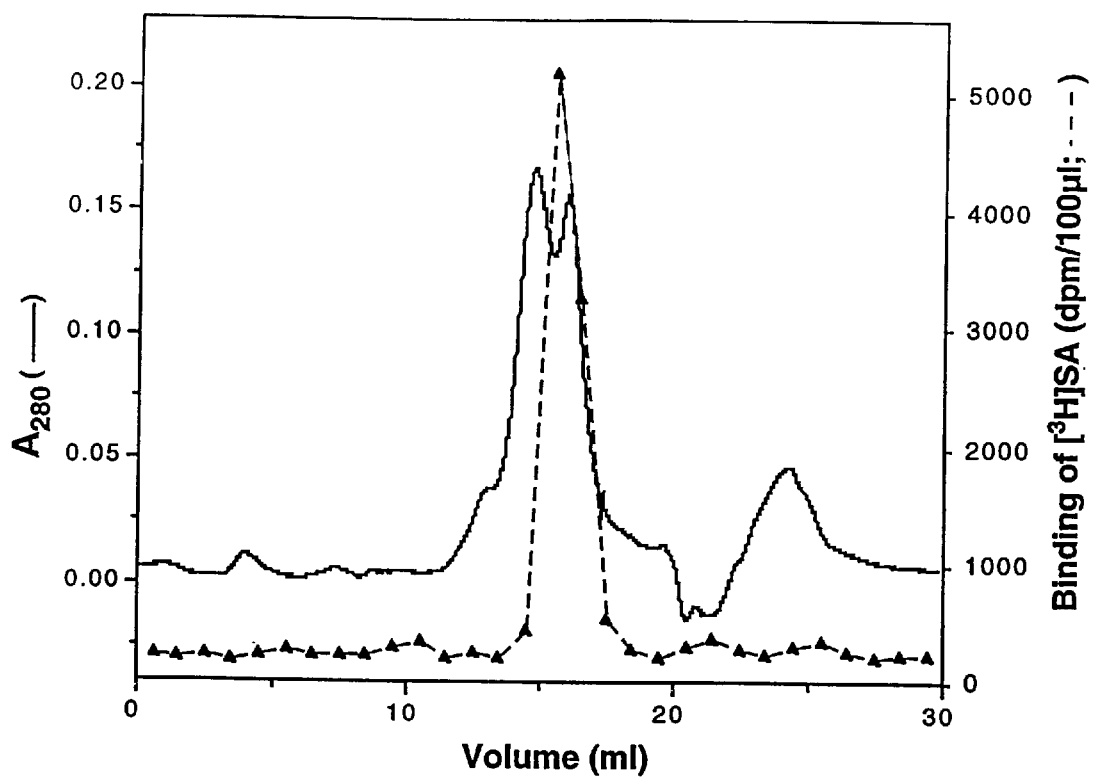
FIG. 9 is a graph showing the elution profiles of the pooled butyl Sepharose fractions following gel filtration chromatography. The pooled butyl Sepharose fractions containing the SA-binding activity were concentrated to 200 μl and loaded onto a Superdex 200 HR column pre-equilibrated in buffer A. Proteins eluted from the column were monitored at 280 nm. Total [$^3$H]SA binding activity (▲) was determined for each fraction and plotted as a dashed line.

As set forth in the Materials and Methods section, SABP2 was further purified. The purification steps utilized included subjecting leaf extracts to 50–75% $(NH_4)_2SO_4$ precipitation, DEAE column chromatography, and butyl sepharose hydrophobic interaction, and Superdex gel filtration chromatography. Fractions (1 ml) were eluted off the butyl Sepharose column and collected and assessed for SA binding activity. Fractions containing SA binding activity were pooled. See FIG. 8. The pooled fractions were concentrated using a Centricon-3 concentrator and loaded onto a Superdex 200 HR gel filtration column. One milliliter fractions were again collected and assayed for SA binding activity. Those samples exhibiting activity were pooled. See FIG. 9. The estimated size of the SABP2 from the gel filtration chromatography is 10–40 kDa which agrees well with the previous results as shown in FIG. 5.

Table 3 shows the stepwise purification factors and recovery of [$^3$H]SA binding activity. This scheme results in a 26 fold purification of [$^3$H]SA binding activity present in the pooled fraction as compared to that in the 50–75% $(NH_4)_2SO_4$ fraction. A further purification factor involving the step from crude leaf extracts to 50–75% $(NH_4)_2SO_4$ fraction is not included in Table 3. This is because the binding activity in the crude extract is too diluted to be measured accurately.

TABLE 3

Partial purification of SABP2

| | Protein (mg) | Total Binding Activity (dpm × 10$^5$) | Recovery (%) | Purification factor (fold) |
|---|---|---|---|---|
| 50–75% $(NH_4)_2SO_4$ | 132 | 8.90 | 100 | 1.0 |
| DEAE | 53 | 6.10 | 68 | 1.7 |
| Butyl Sepharose | 4.4 | 0.85 | 9.6 | 2.9 |
| Superdex 200 | 0.48 | 0.84 | 9.4 | 26 |

Further purification of SABP2 using additional chromatography steps such as affinity chromatography is currently ongoing.

REFERENCES

Abad P, Marais A, Cardin L, Poupet A, Ponchet M (1988) The effects of benzoic acid derivatives on *Nicotiana tabacum* growth in relation to PR-b1 production. Antiviral Res 9: 315–327.

Antoniw J F, White R F (1980) The effects of aspirin and polyacrylic acid on soluble leaf proteins and resistance to virus infection in five cultivars of tobacco. Phytopathol Z 98: 331–341.

Bi Y M, Kenton P, Mur L, Darby R, Draper J (1995) Hydrogen peroxide does not function downstream of salicylic acid in the induction of PR protein expression. Plant J 8: 235–245.

Bowling S A, Guo A, Cao H, Gordon AS, Klessig D F, Dong X (1994) A mutation in Arabidopsis that leads to constitutive expression of systemic acquired resistance. Plant Cell 6: 1845–1857.

Bradford M M (1976) A rapid and sensitive method for the quantitation of microgram quantities of protein utilizing the principle of protein-dye binding. Anal Biochem 77: 248–254.

Cao H, Bowling S A, Gordon A S, Dong X (1994) Characterization of an Arabidopsis mutant that is nonresponsive to inducers of systemic acquired resistance. Plant Cell 6: 1583–1592.

Chamnongpol S, Willekens H, Langebartels C, Van Montagu M, Inze D, Van Camp W (1996) Transgenic tobacco with a reduced catalase activity develops necrotic lesions and induces pathogenesis-related expression under high light. Plant J 10: 491–503.

Chen Z, Klessig D F (1991) Identification of a soluble salicylic acid-binding protein that may function in signal transduction in the plant disease resistance response. Proc Natl Acad Sci USA 88: 8179–8183.

Chen Z, Ricigliano J W, Klessig D F (1993a) Purification and characterization of a soluble salicylic acid-binding protein from tobacco. Proc Natl Acad Sci USA 90: 9533–9537.

Chen Z, Silva H, Klessig D F (1993b) Active oxygen species in the induction of plant systemic acquired resistance by salicylic acid. Science 262: 1883–1886.

Conrath U, Chen Z, Ricigliano J W, Klessig D F (1995) Two inducers of plant defense responses, 2,6-dichloroisonicotinic acid and salicylic acid, inhibit catalase activity in tobacco. Proc Natl Acad Sci USA 92: 7143–7147.

Cutt, J R, Klessig, D F (1992) Salicylic acid in plants: a changing perspective. Pharmacology Technology 16:26–34.

Delaney T P, Uknes S, Vernooij B, Friedrich L, Weymann K, Negrotto D, Gaffney T, Gut-Rella M, Kessmann H, Ward E, Ryals J, Uknes S, Ward E (1994) Systemic acquired resistance. Plant Physiol 104: 1109–1112.

Delaney T P, Friedrich L, Ryals J A (1995) Arabidopsis signal transduction mutant defective in chemically and biologically induced disease resistance. Proc Natl Acad Sci USA 92: 6602–6606.

Dietrich R A, Delaney T P, Uknes S J, Ward E R, Ryals J A, Dangl J L (1994) Arabidopsis mutants simulating disease resistance response. Cell 77: 565–577.

Durner J, Klessig D F (1995) Inhibition of ascorbate peroxidase by salicylic acid and 2,6-dichloroisonicotinic acid, two inducers of plant defense responses. Proc Natl Acad Sci USA 92: 11312–11316.

Durner J, Klessig D F (1996) Salicylic acid is a modulator of tobacco and mammalian catalases. J Biol Chem 271: 28492–28501.

Enyedi A J, Yalpani N, Silverman P, Raskin I (1992) Localization, conjugation and function of salicylic acid in tobacco during the hypersensitive reaction to tobacco mosaic virus. Proc Natl Acad Sci USA 89: 2480–2484.

Friedrich L, Lawton K, Ruess W, Masner P, Specker N, Gut Rella M, Meier B, Dincher S, Staub T, Uknes S, MΘtraux J -P, Kessmann H, Ryals J (1996) A benzothiadiazole derivative induces systemic acquired resistance in tobacco. Plant J 10: 61–70.

Gaffney T, Friedrich L, Vernooij B, Negrotto D, Nye G, Uknes S, Ward E, Kessmann H, Ryals J (1993) Requirement of salicylic acid for the induction of systemic acquired resistance. Science 261: 754–756.

Gorlach J, Volrath S, Knauf-Beiter G, Hengy G, Beckhove U, Kogel K -H, Oostendorp M, Staub T, Ward E, Kessmann H, Ryals J (1996) Benzothiadiazole, a novel class of inducers of systemic acquired resistance, activates gene expression and disease resistance in wheat. Plant Cell 8: 629–643.

Greenberg J T, Guo A, Klessig D F, Ausubel F M (1994) Programmed cell death in plants: a pathogen-triggered response activated coordinately with multiple defense functions. Cell 77: 551–563.

Kakidani and Ptashne (1988) GAL4 activates gene expression in mammalian cells. Cell 52:161–167.

Klessig D F, Malamy J (1994) The salicylic acid signal in plants. Plant Mol Biol 26: 1439–1458.

León J, Lawton M A, Raskin I (1995) Hydrogen peroxide stimulates salicylic acid biosynthesis in tobacco. Plant Physiol 108: 1673–1678.

Leslie C A, Romani R J (1988) Inhibition of ethylene biosynthesis by salicylic acid. Plant Physiol 88: 833–837.

Ma, J. et al. (1988) Yeast activators stimulate plant gene expression. Nature 334:631–633.

Malamy, J, Hennig, J and Klessig, D F (1992) Temperature dependent induction of salicylic acid and its conjugates during the resistance response to tobacco mosaic virus infection. Plant Cell 4: 359–366.

Malamy J, Carr J P, Klessig D F, Raskin I (1990) Salicylic acid: a likely endogenous signal in the resistance response of tobacco to viral infection. Science 250: 1002–1004.

Malamy J, Sánchez-Casas, P, Hennig J, Guo A, Klessig D F (1996) Dissection of the salicylic acid signalling pathway for defense responses in tobacco. Mol Plant-Microbe Interact 9: 474–482.

Métraux J -P, Signer H, Ryals J A, Ward E, Wyss-Benz M, Gaudin J, Raschdorf K, Schmid E, Blum W, Inverardi B (1990) Increase in salicylic acid at the onset of systemic acquired resistance in cucumber. Science 250: 1004–1006.

Neuenschwander U, Vernooij B, Friedrich L, Uknes S, Kessmann H, Ryals J (1995) Is hydrogen peroxide a second messenger of salicylic acid in systemic acquired resistance? Plant J 8: 227–233.

Rasmussen J B, Hammerschmidt R, Zook M N (1991) Systemic induction of salicylic acid accumulation in cucumber after inoculation with *Pseudomonas syringae* pv. *syringae*. Plant Physiol 97: 1342–1347.

Rüffer M, Steipe B, Zenk M H (1995) Evidence against specific binding of salicylic acid to plant catalase. FEBS Lett 377: 175–180.

Ryals J (1994) A central role of salicylic acid in plant disease resistance. Science 266: 1247–1250.

Shah J, Klessig D F (1996) Identification of a salicylic acid-responsive element in the promoter of the tobacco pathogenisis-related β-1,3 glucanase gene, PR-2d. Plant J. 10: 1089–1101.

Shah J, Tsui F, Klessig D F (1997) Characterization of a salicylic acid-insensitive mutant (sai1) of *Arabidopsis thaliana*, identified in a selective screen utilizing the SA-inducible expression of the tms2 gene. Mol Plant-Microbe Interact 10: 69–78.

Summermatter K, Sticher L, Métraux J -P (1995) Systemic responses in *Arabidopsis thaliana* infected and challenged with *Pseudomonas syringae* pv *syringae*. Plant Physiol 108: 1379–1385.

Takahashi H, Chen Z, Du H, Liu Y, Klessig D F (1997) Development of necrosis and activation of disease resistance in transgenic tobacco plants with severely reduced catalase levels. Plant J. 11: 993–1005.

Van Loon L C (1983) The induction of pathogenesis-related proteins by pathogens and specific chemicals. Neth J Plant Pathol 89: 265–273.

Vanlerberghe G C, McIntosh L (1996) Signals regulating the expression of the nuclear gene encoding alternative oxidase of plant mitochondria. Plant Physiol 111: 589–595.

Vernooij B, Friedrich L, Morse A, Reist R, Kolditz-Jawhar R, Ward E, Uknes S, Kessmann H, Ryals J (1994) Salicylic acid is not the translocated signal responsible for inducing systemic acquired resistance but is required in signal transduction. Plant Cell 6: 959–965.

Vernooij B, Friedrich L, Ahl Goy P, Staub T, Kessmann H, Ryals J (1995) 2,6-Dichloroisonicotinic acid-induced resistance to pathogens does not require the accumulation of salicylic acid. Mol Plant-Microbe Interact 8: 228–234.

Wagner A M (1995) A role for active oxygen species as second messengers in the induction of alternative oxidase gene expression in *Petunia hybrida* cells. FEBS Lett 368: 339–342.

White R F (1979) Acetylsalicylic acid (aspirin) induces resistance to tobacco mosaic virus in tobacco. Virology 99: 410–412.

Wobbe K K, Klessig D F (1996) Salicylic acid-an important signal in plants. In Signal Transduction in Plant Growth and Development, D P S Verma, ed., Plant Gene Research Series, Springer-Verlag, Wien and New York, pp. 167–196.

While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. An isolated salicylic acid (SA) binding protein having an apparent relative molecular mass of 25 kDa as determined by gel filtration chromatography, which reversibly binds SA with a Kd of less than about 500 nM and having a Bmax for SA of less than about 100 fmol/mg protein.

2. The protein of claim 1, which binds to SA with a $k_d$ of between about 50 and 250 nM.

3. The protein of claim 1, wherein the $B_{max}$ is about 10 fmol/mg protein.

4. The protein of claim 1, isolated from a plant.

5. The protein of claim 4, isolated from tobacco.

6. The protein of claim 4, isolated from Arabidopsis.

7. The protein of claim 4, which is precipitable from a leaf extract by ammonium sulfate between about 50 and 75% saturation.

* * * * *